(12) United States Patent
Jamnia et al.

(10) Patent No.: US 8,167,616 B2
(45) Date of Patent: May 1, 2012

(54) DENTAL HANDPIECE SYSTEM WITH REPLACEABLE TREATMENT TIPS

(75) Inventors: Mohammad Ali Jamnia, Pleasant Prairie, WI (US); Neville Hammond, Schaumburg, IL (US); Howard Wax, Deerfield, IL (US); Ronald Saslow, Highland Park, IL (US)

(73) Assignee: Hu-Friedy Mfg. Co., LLC, Chicago, IL (US)

( * ) Notice: Subject to any disclaimer, the term of this patent is extended or adjusted under 35 U.S.C. 154(b) by 57 days.

(21) Appl. No.: 12/723,096

(22) Filed: Mar. 12, 2010

(65) Prior Publication Data

US 2011/0223559 A1    Sep. 15, 2011

(51) Int. Cl.
    *A61C 17/00*    (2006.01)
(52) U.S. Cl. ........................................ 433/143
(58) Field of Classification Search ............ 433/80, 433/119, 141, 143; 132/309–311
    See application file for complete search history.

(56) References Cited

U.S. PATENT DOCUMENTS

| 169,003 | A | 10/1875 | Johnston |
|---|---|---|---|
| 233,486 | A | 10/1880 | Donaldson |
| 451,371 | A | 4/1891 | Ennes |
| 610,483 | A | 9/1898 | Fritz |
| 808,992 | A | 1/1906 | Lawson |
| 1,115,057 | A | 10/1914 | Delaney |
| 1,975,877 | A | 10/1934 | Thomas |
| 4,060,897 | A | 12/1977 | Greenstein |
| 4,552,531 | A | 11/1985 | Martin |
| 4,634,376 | A | 1/1987 | Mössle et al. |
| 4,820,154 | A | 4/1989 | Römhild et al. |
| 5,011,319 | A | 4/1991 | Levi et al. |
| 5,100,321 | A | 3/1992 | Coss et al. |
| 5,127,415 | A | 7/1992 | Preciutti |
| 5,328,370 | A * | 7/1994 | Chen ............................. 433/147 |
| 5,816,806 | A | 10/1998 | Herbst et al. |
| 6,015,328 | A * | 1/2000 | Glaser ............................. 446/72 |
| 6,109,918 | A * | 8/2000 | Hammond et al. ........... 433/141 |
| 6,193,515 | B1 | 2/2001 | Rahman |

(Continued)

FOREIGN PATENT DOCUMENTS

SE    9703907 A    4/1999

(Continued)

OTHER PUBLICATIONS

LM-Ergo/Mix product brochure, LM-Instruments Oy (4 sheets).

*Primary Examiner* — Cris L Rodriguez
*Assistant Examiner* — Matthew Seward
(74) *Attorney, Agent, or Firm* — Marshall, Gerstein & Borun LLP

(57) ABSTRACT

A dental hand piece with replaceable tips at either end of a tubular handle, each of the replaceable tips including a tip assembly having an instrument working tip end at a distal end of a main tip body and a shank extending from the instrument working tip end to a proximal end of the main tip body. The tip assembly may be provided with a flat-blade extension end at the proximal end of the main tip body. The flat-blade extension end passes through a keyway-shaped slot provided in a locking component, and engages locking structure provided on a cylindrical barrel member. Replaceable tips at the ends of the tubular handle may be secured in 180° orientation to one another. A spring arm member may additionally or alternatively engage notches along an interior wall of the cylindrical barrel member.

8 Claims, 14 Drawing Sheets

U.S. PATENT DOCUMENTS

| | | |
|---|---|---|
| 6,361,317 B1 | 3/2002 | Rahman |
| 6,619,877 B1 | 9/2003 | Huang |
| 6,716,028 B2 | 4/2004 | Rahman et al. |
| 6,729,877 B2 | 5/2004 | Rahman |
| 6,817,862 B2 | 11/2004 | Hickok |
| 6,997,709 B2 | 2/2006 | Kangasniemi et al. |
| 7,011,520 B2 * | 3/2006 | Rahman et al. ............ 433/86 |
| 7,159,494 B2 | 1/2007 | Jamnia et al. |
| 2002/0096204 A1 | 7/2002 | Lin |
| 2006/0131906 A1 * | 6/2006 | Maurer et al. ............ 294/100 |

FOREIGN PATENT DOCUMENTS

| | | |
|---|---|---|
| WO | WO-9942036 A1 | 8/1999 |
| WO | WO-01/60279 A1 | 8/2001 |

* cited by examiner

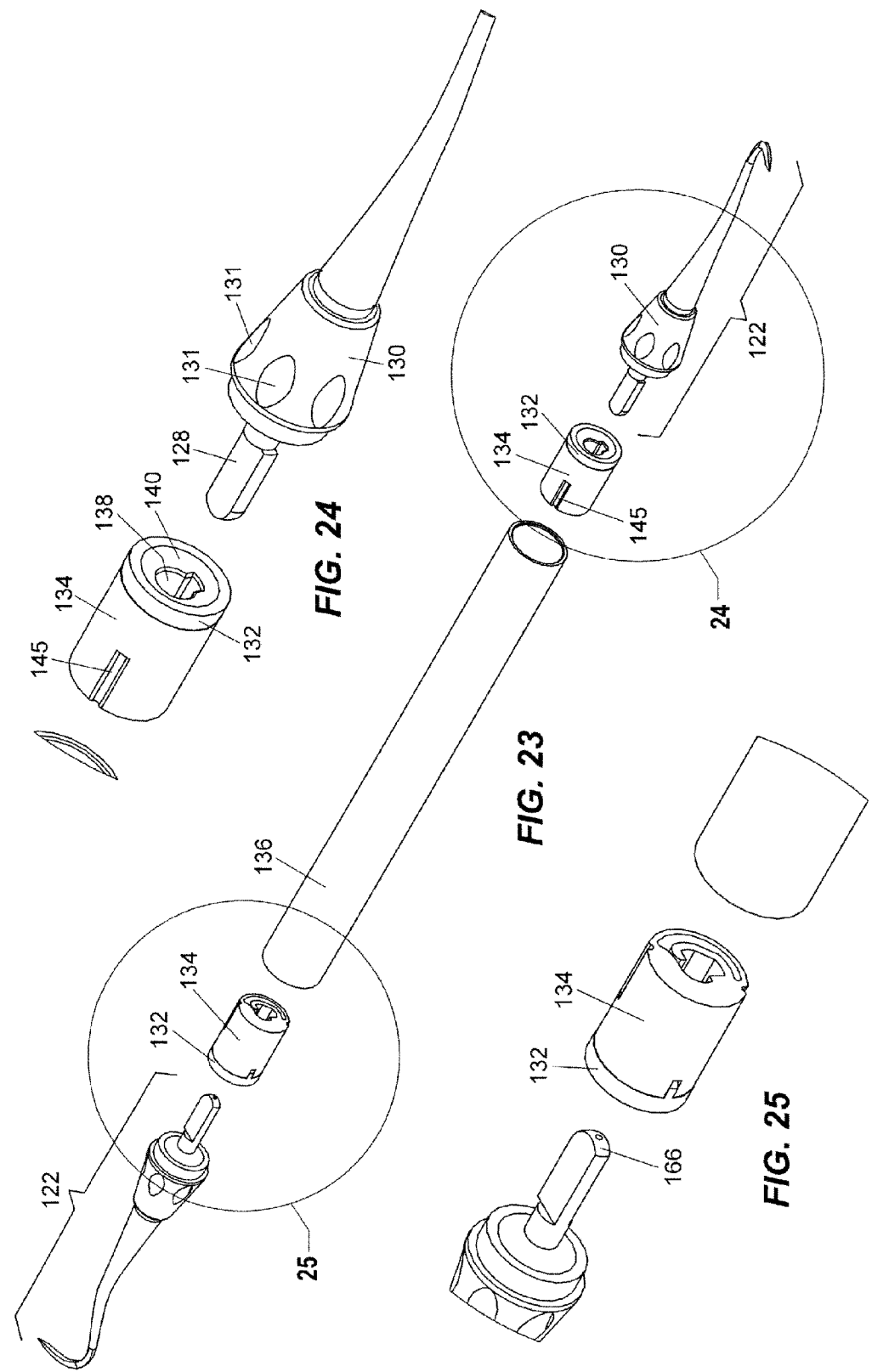

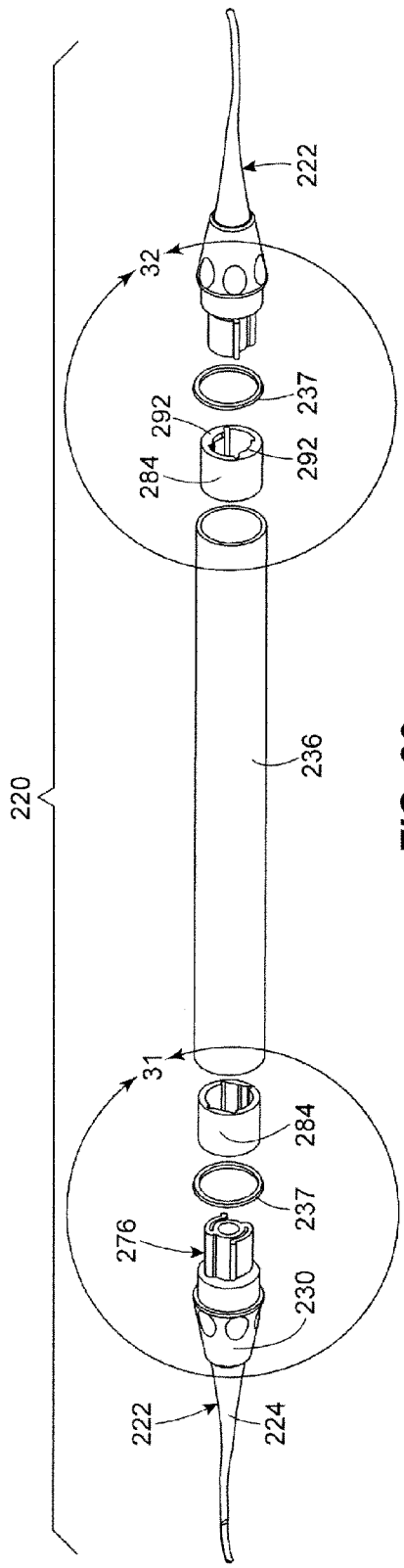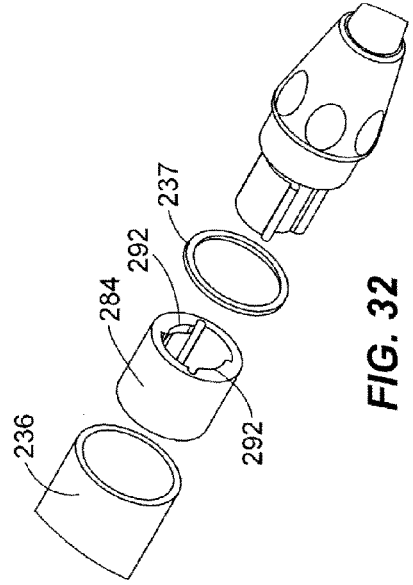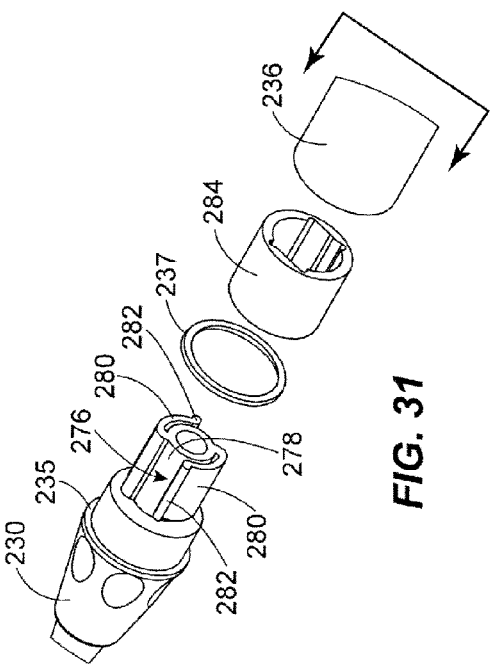

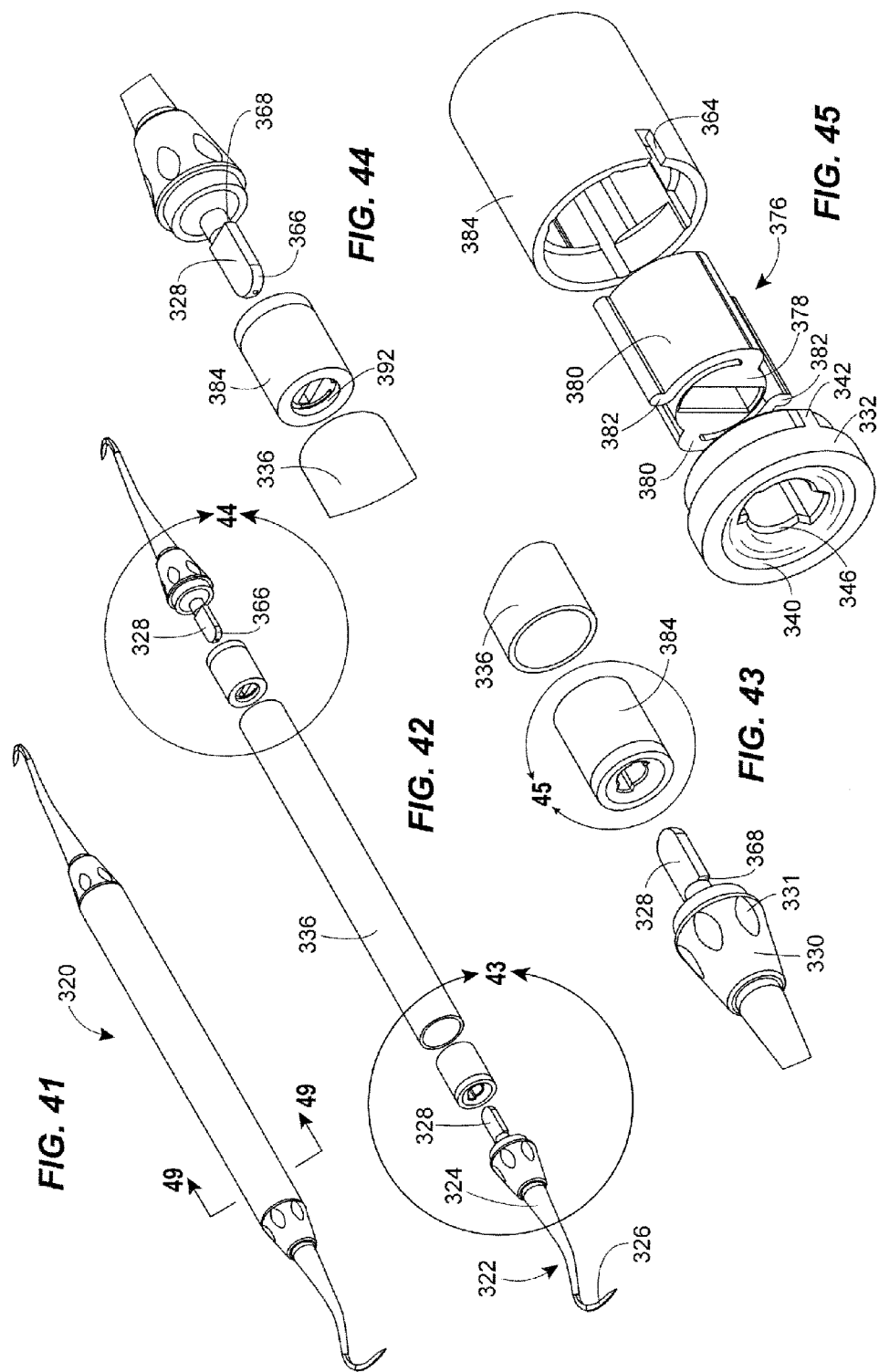

DENTAL HANDPIECE SYSTEM WITH REPLACEABLE TREATMENT TIPS

FIELD OF THE DISCLOSURE

The disclosure pertains to dental instruments and, more particularly, to dental instruments in the form of a hand piece having replaceable and exchangeable treatment tips.

BACKGROUND OF THE DISCLOSURE

Hand-held dental instruments typically include an elongated shaft for gripping and manipulating by the dental practitioner, and a working tool or dental point located at one or both ends of the shaft. The tools or points are normally inserted into cone members carried by the handle which cones have sockets for receiving a base of the tool. Examples of such dental hand-piece constructions can be found in U.S. Pat. Nos. 6,361,317 and 5,816,806.

Problems have developed with authorized (and unauthorized) re-tipping of dental points for such dental hand-piece structures. For example, replacing the working point (also known as re-tipping in the industry) creates several concerns, including that the handle-point interface (i.e., the cone area) may be damaged by the re-tipping process and thereby lower the overall quality of the instrument. In addition, after instruments become dull, they need to be sharpened, but after sharpening a few times, the tip points can lose too much mass and may not be sharpened any longer (or should not be sharpened further, for safety and other reasons). There are also problems associated with procedures for re-tipping, such as where, if a screw-engagement system is used, the blade tips at the respective ends of the handle do not properly or reliably align with one another in an oppositely-directed manner, as is customary with manual dental instruments used for removing tartar, plaque, and other calculus from teeth. Extra time must also be taken to assemble screw-type replacement tips into the handle. There are also the issues of infection control and complications to adequate sterilization. Further, the handling of sharp bio-contaminated instruments is dangerous. There is also the problem of an appropriate way to have used instrument tip points washed, cleaned, sterilized, honed or otherwise reconditioned as needed.

It would be desirable to be able to provide dental instruments with easily replaceable tips that may be safely deposited in sharps containers. In particular, it would be beneficial to provide a system in which, after use, dental instrument tips, such as scaler tips, may be released from a handle directly into a sharps container, and re-sterilized. With such a system, one could have the ability to identify batches of replacement tips for dental hand-piece instruments that have been properly sterilized and are ready to re-tip a standard handle, and/or to identify how many sharpenings have already occurred for a set of replacement tips of a given instrument type.

SUMMARY OF THE DISCLOSURE

A dental instrument includes an elongate generally tubular handle portion, at least one end, and preferably both ends, of which includes a locking mechanism capable of reliably and securely receiving a replaceable tip assembly. The separately replaceable tip assemblies each includes a working instrument tip at the distal end of a main tip body and an attached, preferably over-molded, cone near the proximal end of the main tip body. Extending proximally of the cone of the main tip body, from a tip shank of the main tip body that runs through the cone, is a blade extension end for engagement with one of the locking mechanisms of the handle.

Various embodiments are provided for connecting the blade extension end of the tip shank into a corresponding blade-receiving cylindrical barrel member of the locking mechanism in the elongate handle portion, to allow the blade extension end, and thereby the tip assembly, to interlock with the elongate handle and be properly axially aligned therewith and properly radially oriented.

The dental delivery systems of the present disclosure allow the replacement points to be assembled onto the handle by a dental clinician both safely and ergonomically. Once the point is used, it may be released from the locking mechanism of the elongate handle portion and directly deposited, for example, into a sharps container. Once the sharps container is full, the container may then be sent, for example off-site, for sterilization, sharpening, or other reconditioning, re-packaged, and returned to the owner/dental clinician.

BRIEF DESCRIPTION OF THE DRAWINGS

FIG. 23 is an exploded perspective view of the first alternate embodiment of a dental hand piece of the present disclosure, illustrating a flat blade extension that is asymmetrical relative to a central axis of the replaceable tip, and a complementary asymmetrical keyway-shaped slot of a locking component;

FIG. 24 is an enlarged exploded view of the region designated by the circular line 24 in FIG. 23;

FIG. 25 is an enlarged exploded view of the region designated by the circular line 25 in FIG. 23;

FIG. 30 is an exploded view of a dental hand piece in accordance with a second alternate embodiment of the present disclosure;

FIG. 31 is an enlarged exploded view of the region designated by the circular line 31 in FIG. 30;

FIG. 32 is an enlarged exploded view of the region designated by the circular line 32 in FIG. 30;

FIG. 41 is a perspective view of dental hand piece in accordance with a third alternate embodiment of the present disclosure;

FIG. 42 is an exploded perspective view of the dental hand piece of FIG. 41;

FIG. 43 is an enlarged exploded view of the region of the hand piece of FIG. 41 taken along the circular line 43 in FIG. 42;

FIG. 44 is an enlarged exploded view of the region of the hand piece of FIG. 41 taken along the circular line 44 in FIG. 42;

FIG. 45 is an enlarged exploded view of the region of the hand piece of FIG. 41 taken along the circular line 45 in FIG. 43;

DETAILED DESCRIPTION OF THE PREFERRED EMBODIMENTS

Figure 1:
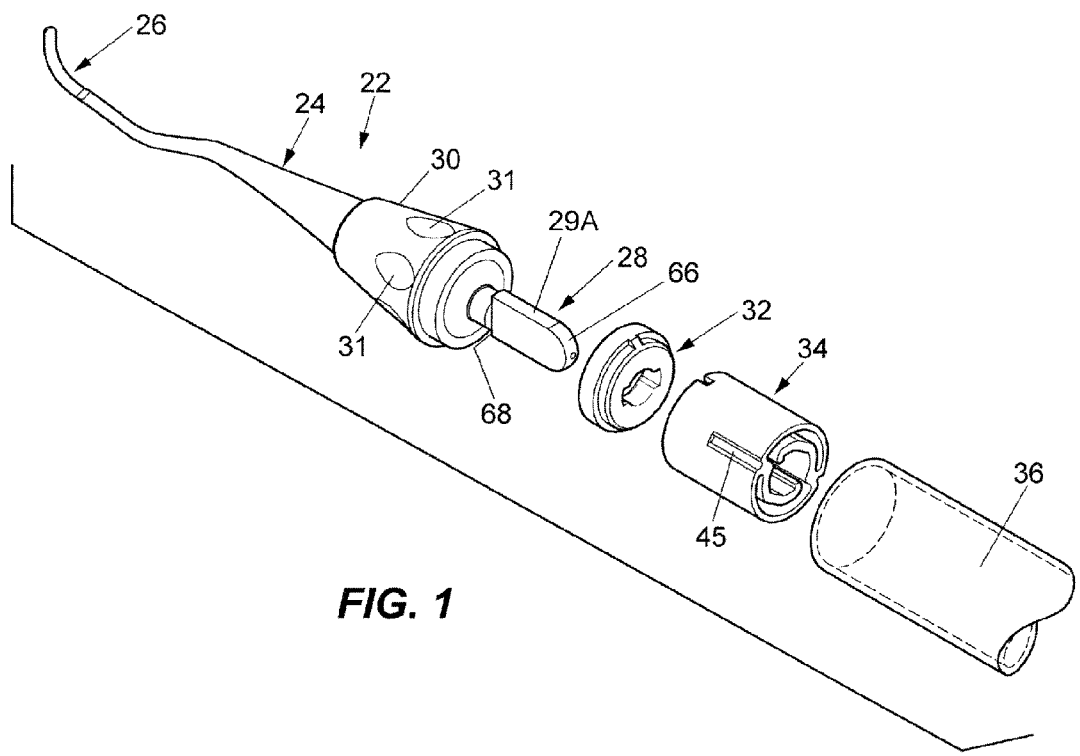
FIG. 1 is an exploded assembly view of a first embodiment of a dental hand-piece instrument made in accordance with the present disclosure, with the tubular handle portion broken away.
Figure 2:
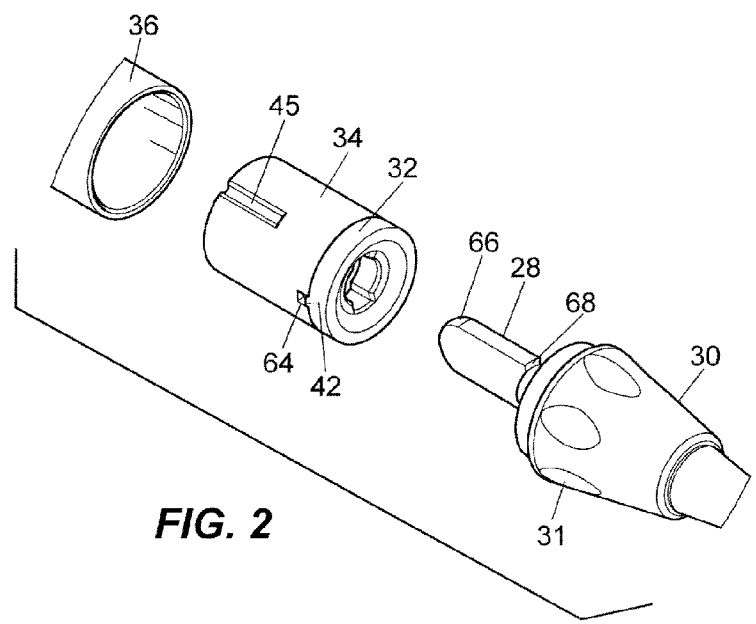
FIG. 2 is an exploded assembly view of the instrument of FIG. 1, viewed from an end opposite to that illustrated in FIG. 1.

While this disclosure is susceptible of embodiments in many different forms, they are illustrated in the drawings and will be described herein in detailed specific embodiments thereof, with the understanding that the present disclosure is to be considered as an exemplification of the principles of the invention and is not intended to limit the invention to the specific embodiments illustrated.

Figure 3:
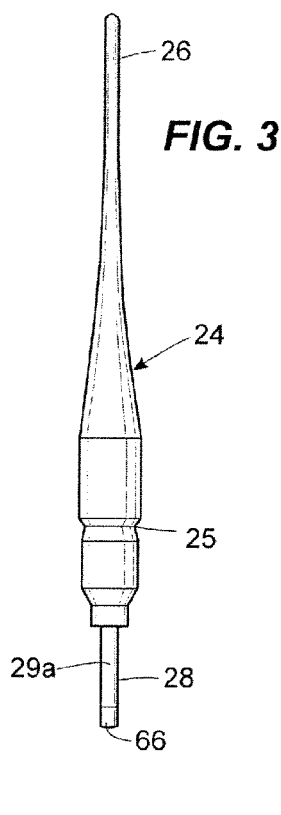
FIG. 3 is a rear view of a replaceable tip component of a replaceable tip assembly for use with the instrument of FIG. 1, with an overmolded cone of the replaceable tip assembly removed for clarity.
Figure 3A:
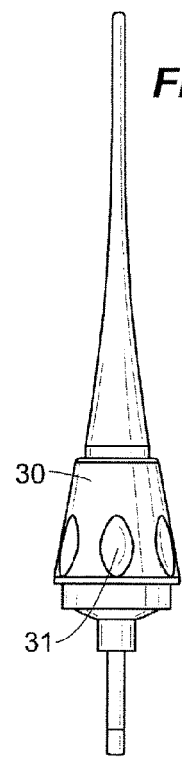
FIG. 3a is a rear view of the replaceable tip component of FIG. 3, including an overmolded cone.
Figure 4:
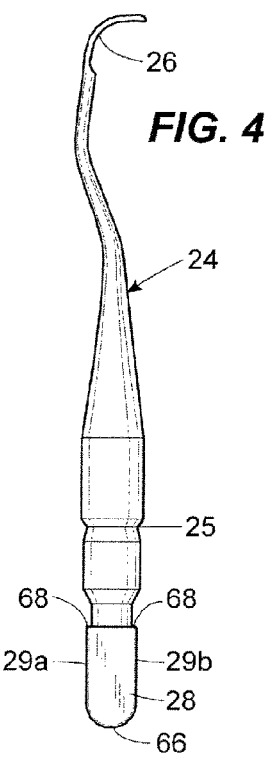
FIG. 4 is a side view of the replaceable tip component of FIG. 3, with the overmolded cone of the replaceable tip assembly removed for clarity.
Figure 4A:
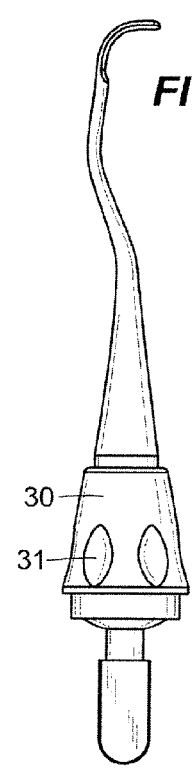
FIG. 4a is a side view of the replaceable tip component of FIG. 3, including an overmolded cone.
Figure 16:
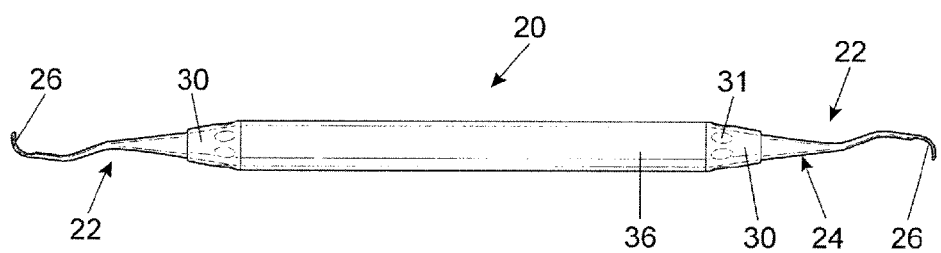
FIG. 16 depicts the fully assembled dental hand piece of the first embodiment of FIG. 1.
Figure 17:
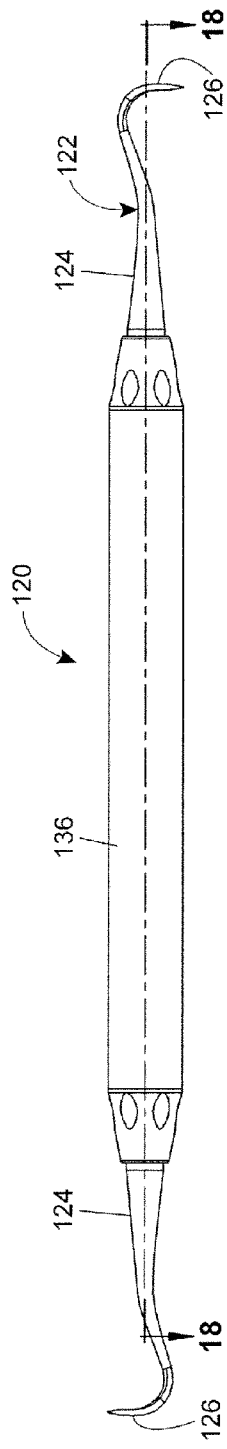
FIG. 17 is a front plan view of a dental hand piece in accordance with a first alternate embodiment of the present disclosure.
Figure 18:
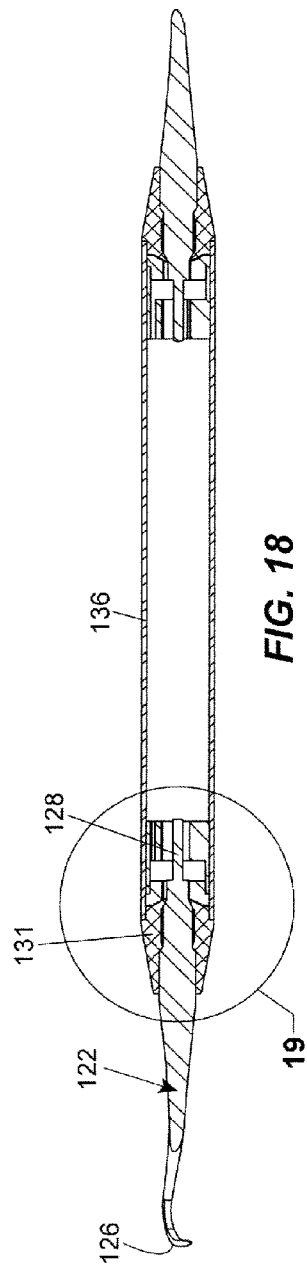
FIG. 18 is a cross-sectional view taken along lines 18-18 of FIG. 17 upon insertion of a blade extension end of the tip shank of the replaceable tip assembly through a keyway of the locking component but prior to rotation of the tip assembly to an orientation in which the blade extension end is out of alignment with the keyway-shaped opening and prior to the blade extension end being in a locked condition relative to the cylindrical barrel component.
Figure 19:
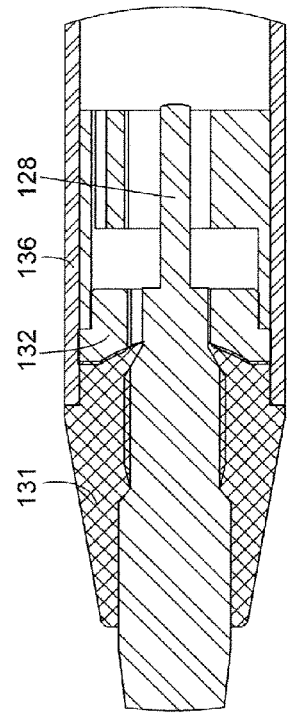
FIG. 19 is an enlarged cross-sectional view of the region designated by the circular line 19 in FIG. 18.
Figure 20:
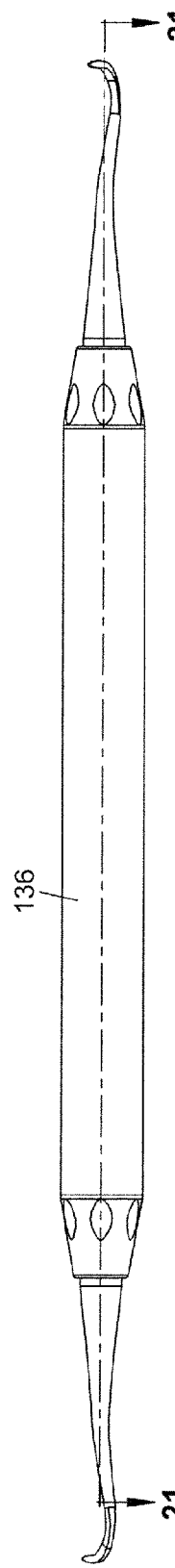
FIG. 20 is a front plan view of the dental hand piece of FIG. 17, upon rotation of the tip assembly so that the blade extension is out of alignment with the keyway opening and in a locked condition relative to the cylindrical barrel component.
Figure 21:
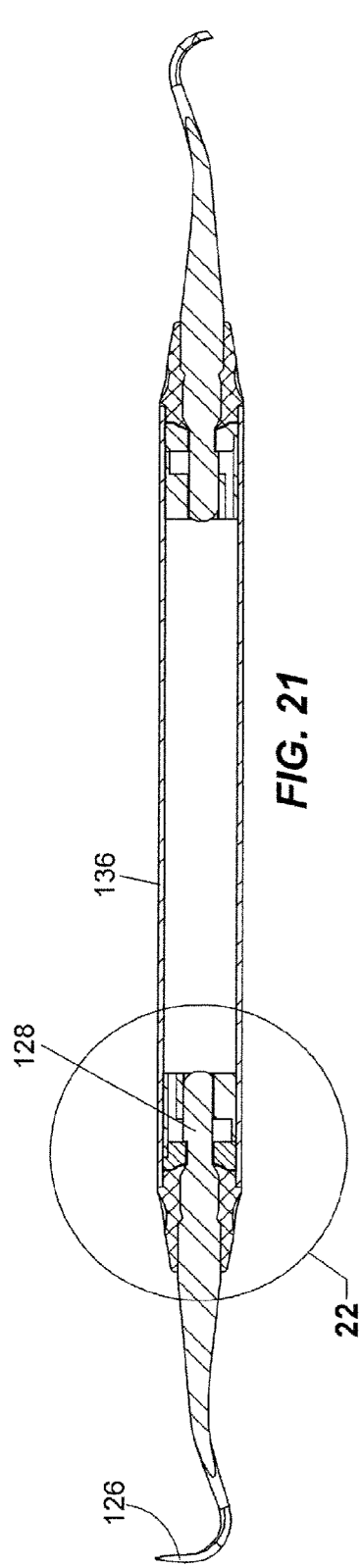
FIG. 21 is a cross-sectional view taken along lines 21-21 of FIG. 20.
Figure 22:
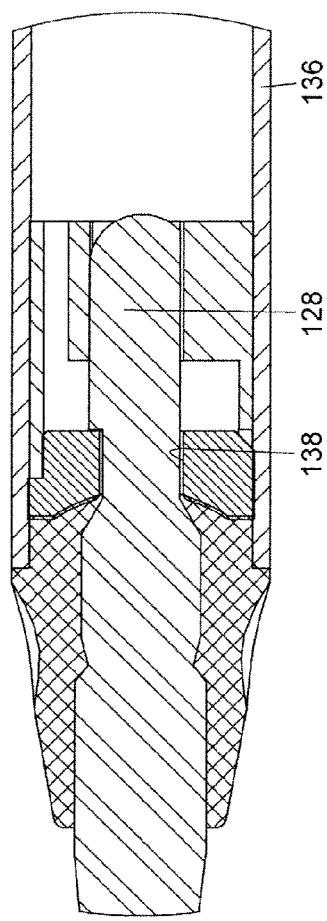
FIG. 22 is an enlarged cross-sectional view of the region designated by the circular line 22 in FIG. 21.

FIG. 16 illustrates a fully assembled dental hand piece of a first embodiment of the present disclosure, as denoted by reference No. 20. Hand piece 20 includes, at one or preferably both ends thereof, a replaceable tip assembly 22 (see FIG. 1) comprising a main tip body 24. As best seen in FIGS. 3 and 4, main tip body 24 includes an instrument working tip end 26 at the distal end and a flat-blade extension end 28 at the proximal end. A cone member 30 (see FIGS. 1, 2, 3a and 4a) may be fixedly attached, for example by overmolding, about a shank portion of the main tip body 24. The cone member 30 preferably has a plurality of radially inwardly-directed dimples (divets or knurl areas) 31 in an outer surface thereof to facilitate gripping and provide a non-slip surface. These dimples 31 may take a myriad of shapes, and in the alternative, may be raised nubs or ribs, or a combination of raised and indented gripping portions may be provided on the cone member 30. The main tip body 24 is preferably made of steel. The cone member 30 is preferably formed of molded thermoplastic material, Silicone, or a modified resin combination including amorphous blends of PPO polyphenylene ether resin and polystyrene (e.g., Noryl resin available from Sabic). During the molding process, the cone member 30 is securely formed in place against, and fixed against rotation about, the main tip body 24. The molded cone member 30 encapsulates an annular notch area 25 formed on a shank of the main tip body 24. The dental hand piece 20 also includes, at one or preferably both ends, a locking component 32 and a blade-receiving cylindrical barrel member 34 that interconnects with the locking component 32. An elongate tubular handle 36 of the dental hand piece 20 receives the blade-receiving cylindrical barrel member 34 and the locking component 32.

Figure 5:
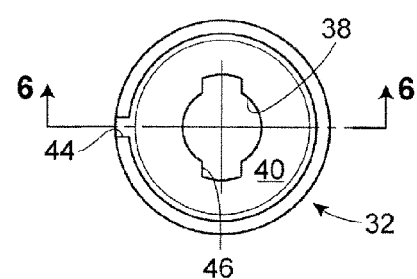
FIG. 5 is a top plan view (viewed from the distal end) of a locking component for use with the instrument of the present disclosure.
Figure 6:
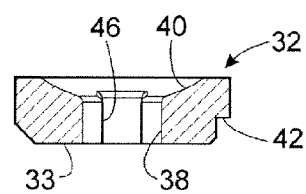
FIG. 6 is a cross-sectional view of the locking component of FIG. 5, taken along lines 6-6 of FIG. 5.

Turning to FIGS. 5 and 6, the locking component 32 is seen as having a configured keyway-shaped slot 38 formed centrally along the axis thereof, and a concave curved surface 40 on a distal side of the locking component 32 surrounding an entrance of the keyway-shaped slot 38. The concave curved surface 40 is exposed when the locking component is securely received in an end of the elongate tubular handle 36, prior to insertion of the flat-blade extension end 28 of a replaceable tip assembly 22. The locking component 32 further includes a seating ledge 42 and an alignment slot 44. The keyway-shaped slot 38 has an elongate keyway 46 formed therein, permitting the flat-blade extension end 28 of the replaceable tip assembly 22 to pass through the keyway-shaped slot 38. When securely received in the end of the elongate tubular handle 36, the keyway-shaped slot 38 is axially aligned with the elongate tubular handle 36.

Figure 7:
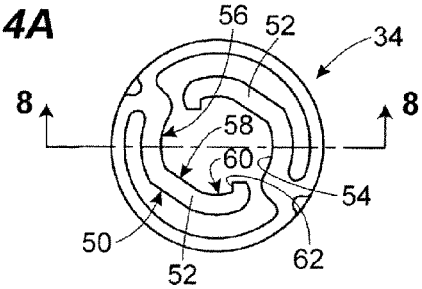
FIG. 7 is an enlarged plan view (viewed from the distal end) of a blade-receiving cylindrical barrel component for use with the instrument of the present disclosure.
Figure 8:
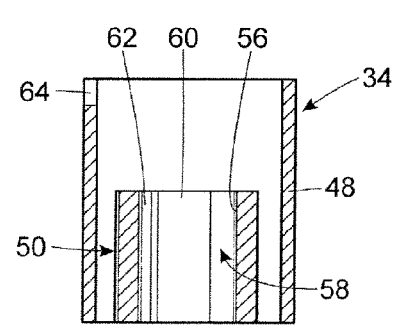
FIG. 8 is a cross-sectional view of the cylindrical barrel component of FIG. 7, taken along lines 8-8 of FIG. 7.
Figure 9:
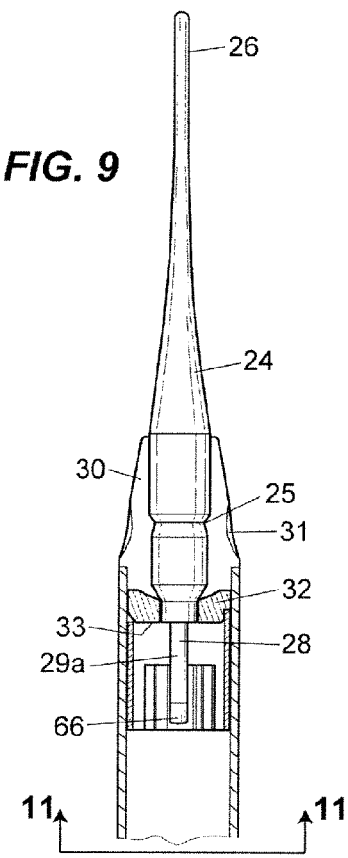
FIG. 9 is a cut-away view of one end of the dental instrument of FIG. 1, upon insertion of a blade extension end of the tip shank of the replaceable tip assembly through a keyway of the locking component but prior to rotation of the tip assembly to an orientation in which the blade extension end is out of alignment with the keyway-shaped opening and prior to the blade extension end being in a locked condition relative to the cylindrical barrel component.
Figure 10:
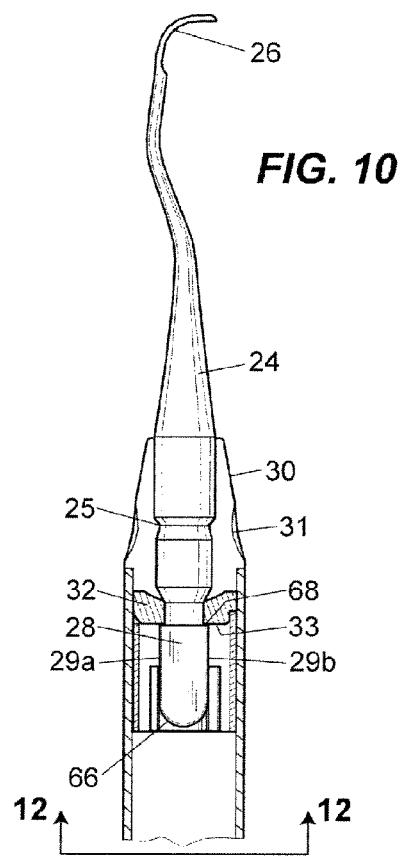
FIG. 10 is a cut-away view of the assembled instrument of FIG. 9, upon rotation of the tip assembly so that the blade extension end is out of alignment with the keyway opening and the blade extension end is in a locked condition relative to the cylindrical barrel component.

As illustrated in FIGS. 7 and 8, the blade-receiving cylindrical barrel member 34 includes an outer wall 48 and a locking assembly 50, the locking assembly 50 comprising a pair of radially-inwardly-projecting, axially-extending resilient locking arms 52. Each of the resilient locking arms 52 may have a shape approximating that of the above-the-dot portion of a question mark (?). The interior wall 54 of each locking arm 52 comprises multiple segments to respectively receive and springably bear against the flat-blade extension end 28 of tip assembly 22. These various wall segments, of interior wall 54, first include an entry segment 56, then a middle locking expansion transfer segment 58, followed by a locking seating segment 60, and finally a lock-stop wall 62. The locking assembly 50 preferably has a shorter axial length than the outer wall 48 of the barrel member 34, such that when the locking component 52 and the blade-receiving cylindrical barrel member 34 are interconnected, the locking assembly 50 is spaced from a proximal underside 33 of the locking component 32. The outer wall 48 of barrel member 34 also includes a notch 64.

Figure 13:
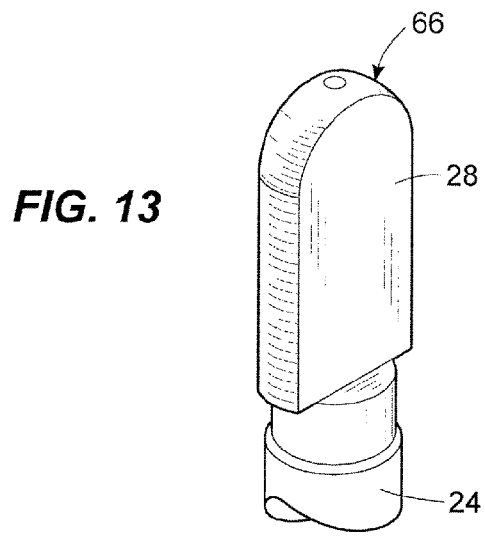
FIG. 13 is a perspective view of the blade extension end of the tip shank of the replaceable tip assembly of FIGS. 3 and 4.
Figure 14:
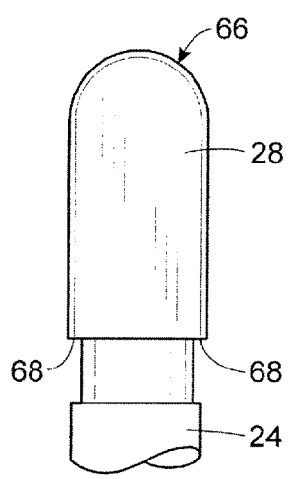
FIG. 14 is a front plan view of the blade extension end illustrated in FIG. 13.
Figure 15:
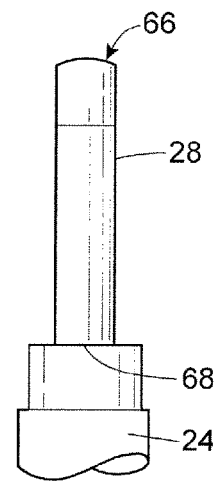
FIG. 15 is a side plan view of the blade extension end illustrated in FIG. 13.

Turning to FIGS. 13-15, it is seen that the flat-blade extension end 28, of the main tip body 24, includes an end 66 on the proximal tip thereof that is curved in two directions, namely, a segment of a three-dimensional ellipsoid or spherical-segment surface, hereinafter a "curved end" 66. The flat-blade extension end 28 is initially formed as a dome-shaped end that is cut down to form the flat-blade extension end 28. Such a curved end surface 66 is useful for effecting the needed assembly engagement with the concave receiving surface 40, i.e., during manipulation and then seating of flat-blade extension end 28 into the keyway-shaped slot 38. The concave receiving surface 40 and the curved surface 66 cooperate with one another to direct the flat-blade extension end 28 into the keyway-shaped slot 38. Flat-blade extension end 28 also includes an undercut ledge 68, the use of which is described below.

Turning to the assembly of a replaceable tip assembly 22 into the tubular handle 36, as seen in FIGS. 1-2 and 9-12, the locking component 32 is first seatably received and engaged into the blade-receiving cylindrical barrel member 34 to form what is referred to herein as a plug, with the seating ledge 42 (of component 32) engaged into the notch area 64 (on barrel member 34). This combination of locking component 32 and barrel member 34 is then properly aligned and then forcibly seated into the handle 36 (due to an interference fit created via the oversized outside diameter of barrel member 34 relative to the internal diameter of handle component 36). Also component 32 and member 34 are specifically radially oriented to the desired alignment position vis-à-vis the handle 36.

In order to effect proper alignment of the lock stop walls 62, 62 of the locking arms 52, 52 of the barrel member 54 with one another so as to achieve the desired 180° orientation of the opposing working tips of an instrument of the present disclosure, the barrel members 54 must be precisely oriented during their installation in the elongate tubular handle 36. The barrel members 54 may be so oriented by use of an assembling fixture (not shown) on which the elongate tubular handle 36 is fixed to a plate. Each of the barrel members 54 is aligned with and secured to a respective locking component 32 to form a plug, and the barrel member 54/locking component 32 plugs are placed on the fixed plate in proper axial alignment with the elongate tubular handle 36 and with one another. The plugs are manipulated, i.e. rotated, until they are in the proper orientation with respect to one another, then a mechanism on the fixture plate is actuated to push the plugs into the respective ends of the elongate tubular handle 36. Each of the cylindrical barrel members 34 may be provided with one or more axially-extending alignment grooves 45 along an exterior surface thereof, to facilitate proper relative orientation of the cylindrical barrel members 34 within the tubular handle 36.

An interference fit may be provided between the barrel members 54, the locking components 52 and the elongate tubular member 36 in order to secure the plugs in place. A braze paste or adhesive material may also be applied to the exterior of the barrel member 34 and locking component 32, and after pushing the plugs into place, the exterior of the elongate tubular member 36 may be heated to secure the plugs in place or to cure the adhesive. With the locking component 32 and barrel member 34 inserted in the handle 36, heat is applied to set the braze paste. Alternately, a metal injection molding process may be used to manufacture the handle 36 and barrel member 34 as an integral unit. When secured in the handle 36, the distal face of locking component 32, which may also be secured by brazing, is seated so as to be generally flush with the outer end of handle member 36.

Figure 11:
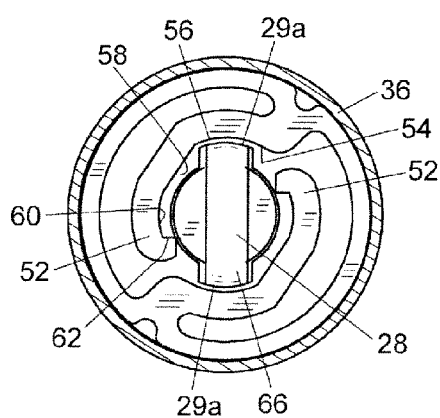
FIG. 11 is a cross-sectional view of the proximal end of the components of the dental hand piece in the condition illustrated in FIG. 9, as viewed along lines 11-11.
Figure 12:
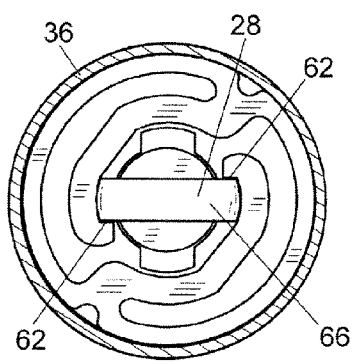
FIG. 12 is a view of the proximal end of the assembled components of the dental hand piece in the condition illustrated in FIG. 10, as viewed along lines 12-12.

The curved end 66 (of flat-blade extension 28) can be inserted into the open end of handle 36, until the surface of the curved end 66 of blade end 28 bears against the concave receiving surface 40 of locking component 32. The tip assembly 22 is then continued to be manipulated until finally, facilitated by contact between the curved end 66 and the concave receiving surface 44, the remainder of flat-blade extension 28 is aligned over and inserted through the elongated keyway 46 of keyway-shaped slot 38. Then, flat-blade extension end 28 is fully extended through keyway 46 until the undercut ledge 68 (on the flat-blade extension end 28) clears the proximal underside 33 of locking component 32. In this condition, the tip assembly 22 is now at least properly axially aligned relative to the elongate tubular handle 36. At this juncture, the tip assembly 22 is then rotated (i.e., counter clockwise, as seen in FIGS. 11 and 12) until the respective undercut ledges 68 of the flat-blade extension end 28 engage and lock against the proximal underside 33 (of locking component 32)—see FIG. 10. Through such rotation, the working point 26, of main tip body 24, is moved a full 90 degrees (from its insertion assembly orientation in FIG. 9 to its relocated and locked orientation in FIG. 10).

Importantly, note FIGS. 11 and 12, during such rotation of tip assembly 22, the outer curved side edges 29A, 29B of flat-blade extension end 28 slideably bear against the inner surfaces (i.e., wall segment portions 56, 58, and 60) of the respective locking arms 52 (of barrel member 34). More specifically, as the blade extension end 28 rotates counterclockwise (compare FIGS. 11 and 12), the curved edges 29A, 29B respectively engage first against the entry segment 56, then locking expansion transfer segment 58, then locking seating segment 69, whereupon further rotation of the blade extension end 28 (and hence tip assembly 22) is prevented by the respective lock-stop walls 62. In this fully rotated and "locked" position, for replaceable tip assembly 22 relative to the tubular handle 36, the interface of undercut ledges 68 with the proximal underside 33 of the locking element 32 prevents any axial movement of the tip assembly 22 relative to the handle 36. Further, the locking engagement of respective curved side edges 29A, 29B with the respective locking seating wall segment 60 (of locking arms 52), as well as the abutting engagement of the blade extension end 28 against the respective lock-stop wall 62, further prevents any radial rotation of tip assembly 22 relative to tubular handle 36.

Thus, with such locked engagements, the replaceable tip assembly 22 is now locked in place, relative to the handle 36, in both proper axial and radial orientations, for use by the dental practitioner. Similarly, at the other end of the handle 36, an equal but oppositely-aligned tip assembly 22 is appropriately inserted, rotated and locked in place, along the same lines as described above, until, as shown in FIG. 16, the entire dental hand piece 20 is configured. In this manner, the respective tip assemblies 22, at the opposite ends of the handle 36, are in oppositely-aligned and locked orientations, ready for use. It will be noted that the lock stop walls 62, 62 of the locking arms 52, 52 of barrel member 54 are preferably positioned such that when the respective blade extension ends 28, 28 (of two opposing tip assemblies) are fully inserted and secured in position, the outer working points 26, 26 are presented in exact alignment, but pointed in opposite directions, oriented 180° with respect to one another. This then is just like opposing end tips of conventional dental hand pieces, i.e., those with permanently-mounted working tips, are expected to have.

In order to facilitate initial insertion of each of a pair of the replaceable tip assembly 22 into the respective ends of elongate tubular handle 36, indicia, such as in the form of an alignment dot on the exterior of the cone member 30 of each of the replaceable tip assemblies 22, and a corresponding pair of alignment dots on the exterior of the elongate tubular handle 36, one at each end, but offset 180° from one another, may be provided. As described further, below, in an alternate embodiment the keyway-shaped slot 38 of the locking component 32, as well as the flat-blade extension end 28, may be asymmetrical, such that the flat-blade extension end 28 only fits through the keyway-shaped slot 38 of the locking component 32 in one orientation. The asymmetrical keyway-shaped slots 38 of the locking components 32 at either end of a given elongate tubular handle 36 may be arranged offset 180° from one another, such that when tip assemblies 22 are engaged with the locking arms 52 of the two barrel members 34, the desired 180° offset orientation of the instrument tips is achieved.

If desired, a scaler tip (such as is depicted in the drawings for tip assembly 22) can be securely, but removably, engaged at one end of the handle using the system of the present disclosure, while a different dental working tip (e.g., a Gracey curette, Universal curette, probe, or mirror—none shown) can be securely, but removably, engaged at the other end of the hand piece 20. That way, a dental clinician can customize his or her own set of dental hand-piece instruments in the manner they personally find most effective for their practices, either having the same type dental tip at each end of a hand piece or, instead, having different hand pieces with different combinations of tips at each end, or with even different sizes thereof. In any event, the locking arrangement as described above always assures that the respective tip assemblies 22 are in equal but oppositely-aligned orientations, such that no one tip assembly 22 can be misaligned within the handle 36 vis-à-vis the tip assembly 22 at the opposite end.

When the tip assembly 22 is interlocked with the barrel member 34, the base of the cone member 30 is flush with the distal end of the locking component 32. Alternately, an o-ring 35, such as a silicone o-ring, may be disposed between the base of the cone member 30 and the distal end of the locking component 32.

Shown in FIGS. 17-29 is a first alternate embodiment of the dental hand piece with replaceable tips of the present disclosure, which hand piece is generally denoted by reference numeral 120. The tip assembly 122 of this first alternate embodiment includes a main body 124 with an instrument working tip end 126 at a distal end thereof, and a flat-blade extension end 128 that is asymmetrical relative to a central axis of the tip assembly 122. The asymmetrical flat-blade extension end 128 passes through a complementary asymmetrical keyway-shaped slot 138 provided in a locking component 132. In this manner, the flat-blade extension end 128 can only be inserted in the keyway-shaped slot 138 in one direction, ensuring proper orientation of the working instrument tip 126 of the tip assembly 122 relative to a working instrument tip of another tip assembly 122 engaged at an opposite end of an elongate tubular handle 136. This avoids the need for the use of indicia, such as alignment dots, on a cone member 130 or on an elongate tubular handle 136. The tip assembly 122 also includes an overmolded cone member 130, preferably including a plurality of divets or inwardly-directed dimples 131 on an outer surface thereof to facilitate gripping.

Like the locking component 32 of the first embodiment described above, the locking component 132 preferably includes a concave distal-facing surface 140 (see FIG. 24), and the flat-blade extension end 128 includes a proximal tip thereof that is curved in two directions, namely, a segment of a three-dimensional ellipsoid or spherical-segment surface, hereinafter a "curved end" 166, the flat-blade extension end 128 being initially formed as a dome-shaped end that is cut down to form the flat-blade extension end 128. The curved end 166 cooperates with the concave distal-facing surface 140 of the locking component 132 to facilitate insertion of the flat-blade extension end 128 through the keyway-shaped slot 138.

Figure 26:
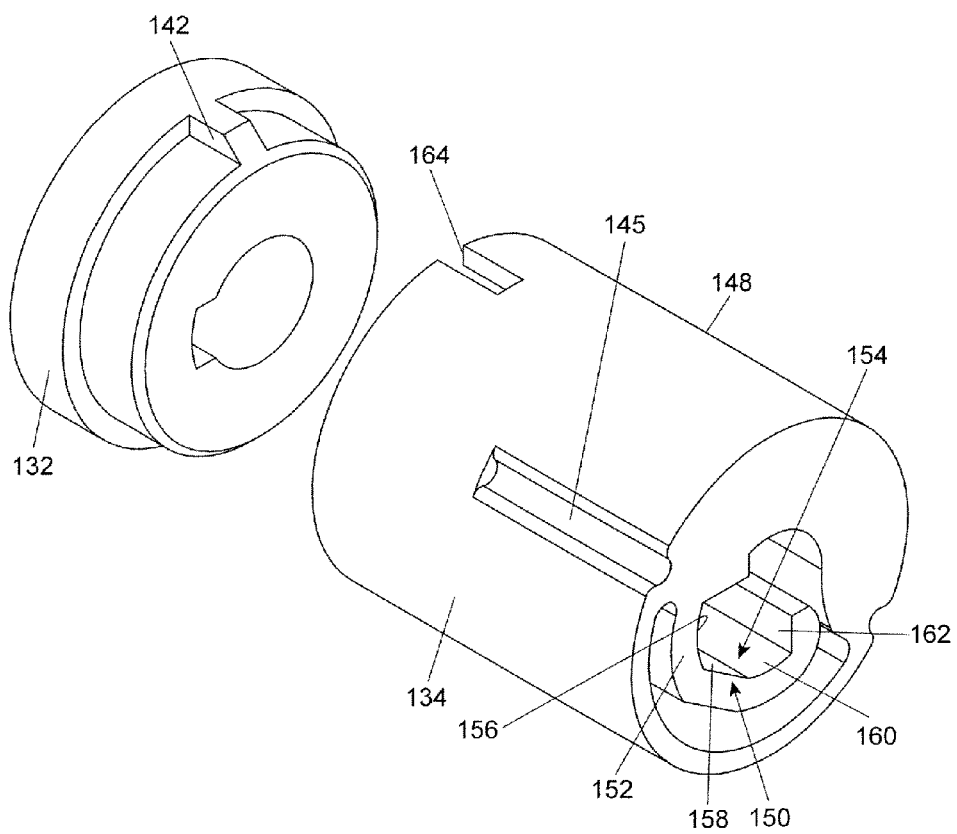
FIG. 26 is an enlarged exploded view of a locking component and respective cylindrical barrel member of the first alternate embodiment, which cooperate to form a plug received in an end of the tubular handle member.
Figure 27:
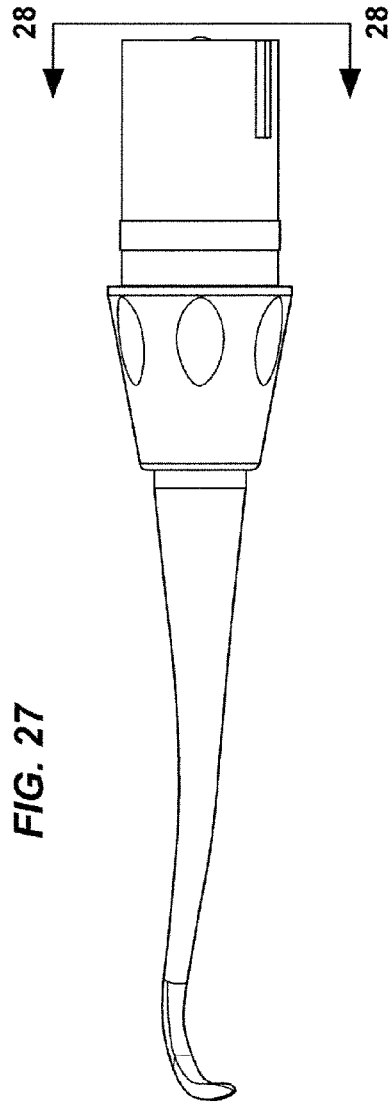
FIG. 27 is a plan view of a replaceable tip insert engaged with a locking component and cylindrical barrel member of the first alternate embodiment of the present disclosure.
Figure 28:
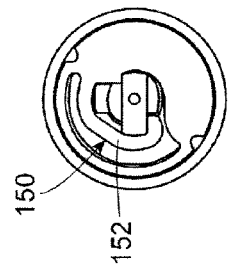
FIG. 28 is an end view, taken along lines 28-28 of FIG. 27.
Figure 29:
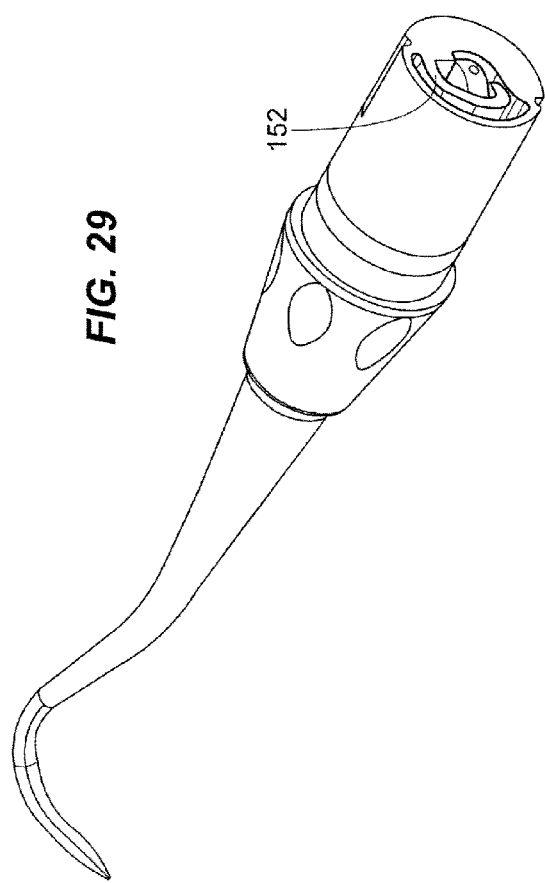
FIG. 29 is a perspective view of the engaged replaceable tip, locking component and cylindrical barrel member of FIG. 27, illustrating the flat-blade extension end of the replaceable tip rotated to a locked condition relative to the cylindrical barrel member.

As illustrated in FIG. 26, the blade-receiving cylindrical barrel member 134 includes an outer wall 148 and a locking assembly 150. While sharing similarities with the locking assembly 50 of the first embodiment described above, the locking assembly 150 comprises a single radially-inwardly-projecting, axially-extending resilient locking arm 152. The resilient locking arm 152 may have a shape approximating that of the above-the-dot portion of a question mark (?). The interior wall 154 of the locking arm 152 comprises multiple segments to respectively receive and springably bear against the flat-blade extension end 128 of tip assembly 122. The various wall segments, of interior wall 154, first include an entry segment 156, then a middle locking expansion transfer segment 158, followed by a locking seating segment 160, and finally a lock-stop wall 162.

Because the flat-blade extension end 128 is asymmetrical relative to the central axis of the tip assembly 122, the flat-blade extension end 128 extends radially (relative to that central axis) in one direction greater than in an opposite direction, rendering a second locking arm unnecessary. Thus, the remainder of the locking assembly 150 (i.e., the portion that is occupied by a second locking arm 52 in the locking assembly 50 of the above-described first embodiment) may be solid.

The locking component 132 is provided with a seating ledge 142 that is received in a complementary notch 164 provided in the blade-receiving cylindrical barrel member 134 to facilitate securement of the locking component 132 and barrel member 134 to one another, forming a plug.

One such locking component 132 and blade-receiving cylindrical barrel members 134 is secured in each end of the elongate tubular handle 136, with the keyway-shaped slot 138 of the locking component 132 at one of the ends having an opposite orientation to (i.e., offset 180° from) the keyway-shaped slot 138 at the other end, with paths defined by the locking arms 152 of the cylindrical barrel members 134 extending in opposite directions from one another. In this manner, when rotated to a locked position, the working instrument tip of the tip assembly 122 is properly oriented in an axially-aligned, but 180° offset position relative to a working instrument tip 126 of another tip assembly 122 engaged at the opposite end of an elongate tubular handle 136. As described above with respect to the first embodiment, the locking components 132 and blade-receiving cylindrical barrel members 134 may be secured in the elongate tubular handle 136 with the assistance of a fixture plate to ensure proper relative orientation. Each of the cylindrical barrel members 134 may also be provided with one or more axially-extending alignment grooves 145 along an exterior surface thereof, to facilitate proper relative orientation of the cylindrical barrel members 134 within the tubular handle 136.

Turning now to FIGS. 30-40, a second alternate embodiment of the dental hand piece with replaceable tips of the present disclosure is illustrated. The hand piece of this embodiment is denoted by reference numeral 220. The dental hand piece 220 preferably includes replaceable tip assemblies 222 at each end thereof. Like the tip assemblies of the previously-described embodiments, each tip assembly 222 includes a main tip body 224 with an instrument working tip end 226 at the distal end thereof and an overmolded cone member 230 provided on a proximal end portion of a shank defining a proximal end of the main tip body 224. In this embodiment, a spring arm member 276 is provided as an extension of the shank at a proximal end of the main tip body 224. The spring arm member 276 comprises a body portion 278 having at least two resilient spring arms 280. A lock stop ridge 282 is provided at the end of each of the resilient spring arms 280.

The spring arm member 276 is lockingly received in a cylindrical barrel member 284 that is provided in an end of an elongate tubular handle 236 of the hand piece 220. The cylindrical barrel member 284 may be secured in the elongate tubular handle 236 with an interference fit. Alternately, a brazing process or adhesive process may be used to secure the cylindrical barrel member 284 within the elongate tubular handle 236, in which a braze paste or adhesive is applied to the exterior of to cylindrical barrel member 284 and/or to the interior of the portion of the elongate tubular handle 236 into which the cylindrical barrel member 284 is to be secured. With the barrel member 284 inserted in the elongate tubular handle 236, heat is applied to set the braze paste or cure the adhesive. Alternately, a metal injection molding process may be used to manufacture the elongate tubular handle 236 and cylindrical barrel member 284 as an integral unit.

Figure 35:
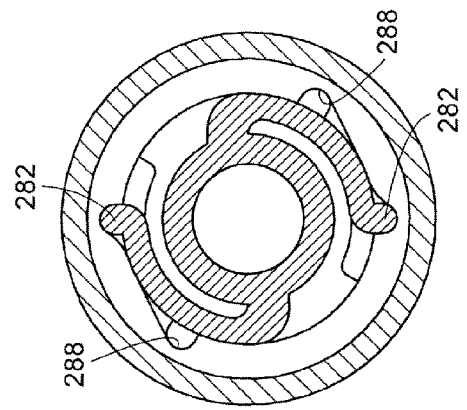
FIG. 35 is a cross-sectional view similar to FIGS. 33 and 34, illustrating the spring arm member of the replaceable tip assembly of the second alternate embodiment in the locked condition.
Figure 34:
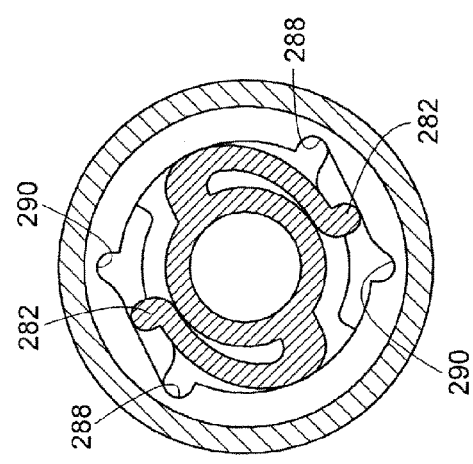
FIG. 34 is a cross-sectional view similar to FIG. 33, illustrating the spring arm member during rotation from the unlocked condition illustrated in FIG. 33, toward a locked condition.
Figure 33:
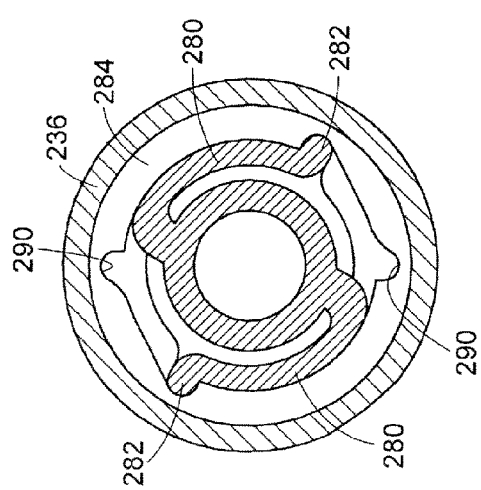
FIG. 33 is a cross-sectional view taken along lines 33-33 of FIG. 32, illustrating a spring arm member of a replaceable tip assembly of the dental hand piece of the second alternate embodiment upon insertion, in an initial unlocked condition relative to a cylindrical barrel member provided in an elongate tubular handle of the dental hand piece.
Figure 36:
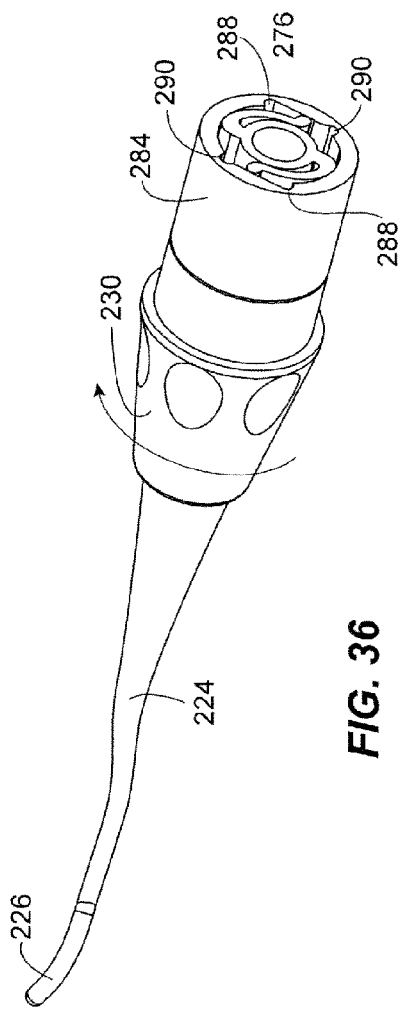
FIG. 36 is a perspective view of a replaceable tip insert of the second alternate embodiment of FIG. 30, with its spring arm member engaged with a cylindrical barrel member, during rotation of the spring arm member from the unlocked condition toward the locked condition, as indicated by the curved directional arrow along the overmolded cone of the replaceable tip insert.
Figure 37:
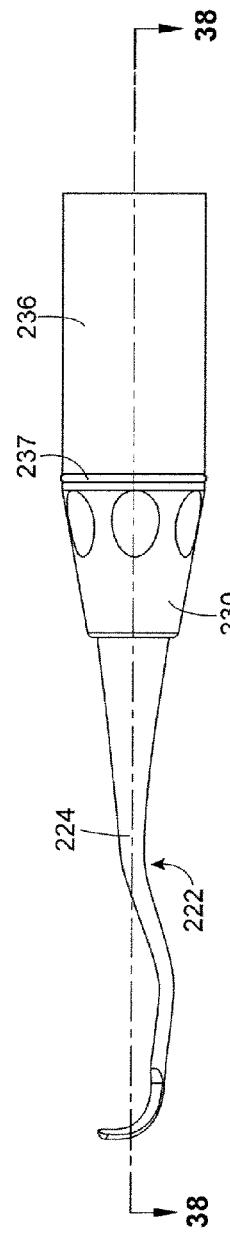
FIG. 37 is an enlarged plan view, broken away, of the dental hand piece of FIG. 30, upon initial insertion of the tip assembly into the elongate tubular handle.
Figure 38:
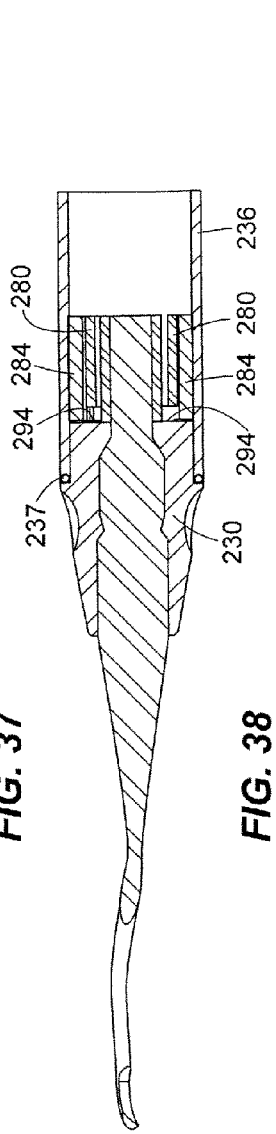
FIG. 38 is a cross-sectional view taken along lines 38-38 of FIG. 37.
Figure 39:
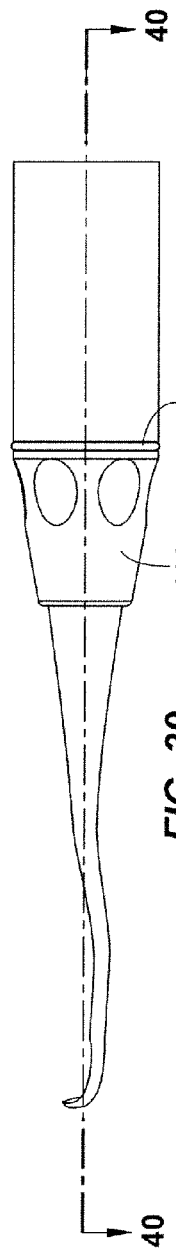
FIG. 39 is an enlarged plan view, broken away, of the dental hand piece of FIG. 30, illustrating the tip assembly rotated along its axis 90° from the initial position illustrated in FIG. 37, to a position such that a spring arm member of the tip assembly is in locking engagement with a cylindrical barrel member provided in the elongate tubular handle.
Figure 40:
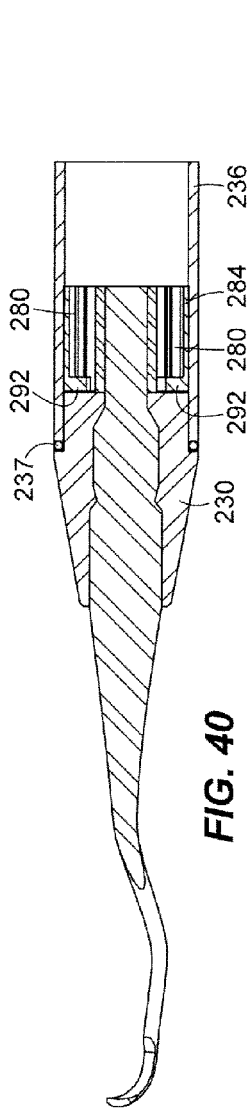
FIG. 40 is a cross-sectional view taken along lines 40-40 of FIG. 39, illustrating the resilient spring arms of the spring arm member being retained in the cylindrical barrel member by a pair of radially-inwardly-directed locking lips provided on a distal end of the cylindrical barrel member.
Figure 46:
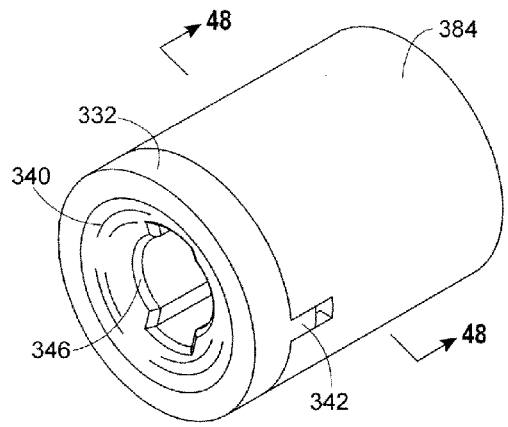
FIG. 46 is a perspective view of a blade-receiving end of the locking component, engaged with a cylindrical barrel member, illustrated in FIG. 45.

As illustrated in FIGS. 33, 34 and 35, the spring arm member 276 is received in an internal opening of the cylindrical barrel member 284, which is provided with a plurality of axially-extending notches 288, 290. Upon insertion, each of the lock stop ridges 282 of the spring arm member 276 is releasably received in a respective one of a first pair of notches 288. Upon rotation from the initial unlocked insertion orientation toward a locked orientation (as indicated by the curved arrow in FIG. 36), each of the resilient spring arms 280 travels radially inwardly along a gradual ramp that forms a cam track along an internal wall of the cylindrical barrel member 284 (as illustrated in FIG. 34) beginning at an exit side of the first pair of axially-extending notches 288, ultimately coming to a stop in a respective one of the pair of notches 290. As the spring arm member 276 rotates toward the locked orientation, each of the resilient spring arms 280 passes under a respective radially-inwardly-directed locking lip 292 (see FIG. 32) provided on a distal end of the cylindrical barrel member 284. There is a small gap (best seen in FIG. 38) provided between a distal end of each of the resilient spring arms 280 and a proximal end surface 294 of the overmolded cone member 230 of the main tip body 224 from which the spring arm member 276 extends, in order to provide sufficient clearance for the locking lips 292 of the cylindrical barrel member 284 to fit between the resilient spring arms 280 and the proximal end surface 294 of the overmolded cone member 230 provided on the main tip body 224. Between the stepped portion 235 of the overmolded cone member 230 and the distal end of the elongate tubular handle 236, a sealing gasket in the form of an o-ring 237 may be provided. The other embodiments described herein may also be provided with similar sealing gaskets.

As best illustrated in FIGS. 33-35, the pair of notches 290 are provided with an entry having a steeper slope than the gradual ramp experienced by the lock stop ridges 282 of the resilient spring arms 280 as they rotate away from the notches 288 toward the notches 290. Once the lock stop ridges 282 pass the steeper slope and the respective resilient spring arms 280 recoil radially outwardly, the lock stop ridges 282 come to rest in the notches 290, preventing further rotation of the spring arm member 276 within the cylindrical barrel member 284. Rotation back toward the initial unlocked orientation is also impeded, i.e., resisted, as the resilient spring arms 280 first have to compress radially inwardly in order for the lock stop ridges 282 to overcome the relatively steep slope at the entry of the notches 290 before the lock stop ridges 282 can ride along the more gradual ramp or cam track back toward the notches 288. A tactile sensation and/or an audible clicking sound may be experienced by the dental technician upon the lock stop ridges 282 coming to rest in the notches 290, confirming the locking of the tip assembly 222 with respect to the elongate tubular handle 236. Although rotation back out of the locked orientation toward the unlocked orientation is restrained by the relatively steep slope at the entry of the notches 290, such rotation is still possible. It merely requires applying a deliberate twisting force to the tip assembly 222 relative to the elongate tubular handle 236, sufficient for the resilient spring arms 280 to compress radially inwardly enough for the lock stop ridges 282 to overcome the relatively steep slope at the entry of the notches 290.

FIGS. 41-49 illustrate a dental hand piece 320 of a third alternate embodiment of the present disclosure. This dental hand piece 320 is a hybrid of the concepts described above with respect to the flat blade extension end 28 of the hand piece 20 of the first embodiment and the spring arm member 276 of the hand piece 220 of the second alternate embodiment, described above. As illustrated in FIGS. 42 and 43, a tip assembly 322 of the hand piece 320 includes a main tip body 324, an instrument working tip end 326, a flat blade extension end 328 having a curved end surface 366, and an overmolded cone member 330, having, for example, dimples (divets or knurl areas) 331 to facilitate gripping.

As best illustrated in FIGS. 45-49, the hand piece 320 of this third alternate embodiment also includes a locking component 332 formed identically to the locking component 32 of the first embodiment, including a concave surface 340 and a keyway 346. A notched cylindrical barrel member 384 is formed as a generally cylindrical tubular member having axially-extending notches 388, 390 formed on its inner wall. A spring arm member 376 comprises a body portion 378 having at least a pair of resilient spring arms 380. A lock-stop ridge 382 is provided at the end of each of the resilient spring arms 380. Body portion 378 has a central generally rectangular axially-extending blade receiving slot 355 to receive the correspondingly-shaped flat-blade extension in 328 of the tip assembly 322. Spring arm member 376 is initially inserted into the cylindrical barrel member 384, and then rotated to align the blade receiving slot 355 with the keyway 346 of locking component 332.

As in the first embodiment, the locking component 332 may be provided with a seating ledge 342 that is received in a complementary axially-extending notch 364 in the cylindrical barrel member 384 to facilitate proper registration of the locking component 332 with the cylindrical barrel member 384. To complete the assembly of the elongate tubular handle 336 and related components, the locking component 332 is interference fit with the cylindrical barrel member 384, and then the locking component 332 and the cylindrical barrel member 384 are assembled via interference fit into the elongate tubular handle 336 of the hand piece 320. Alternately, a brazing process may be used to secure the cylindrical barrel member 384 within the elongate handle 386, in which a braze paste or adhesive is applied to the exterior of the cylindrical barrel member 384 and/or to the interior portion of the elongate tubular handle 336 in which the barrel member 384 is to be secured. With the barrel member 384 inserted in the elongate tubular handle 336, heat is applied to set the braze paste or cure the adhesive. Alternately, a metal injection molding process may be used to manufacture the elongate tubular handle 336 and cylindrical barrel member 384 as an integral unit. When secured in the elongate tubular handle 336, the distal face of locking component 332, which may also be secured by brazing or adhesive, is seated so as to be generally flush with the outer end of handle member 386.

Figure 47:
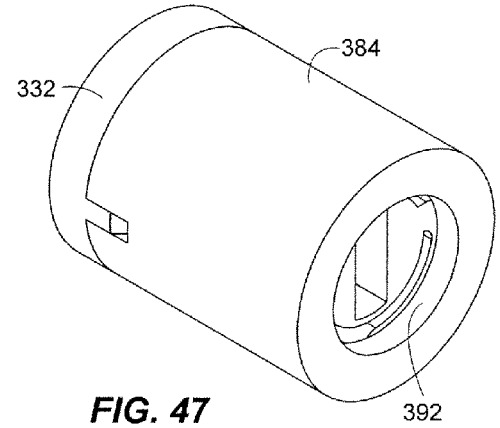
FIG. 47 is a perspective view of an end of the cylindrical barrel member illustrated in FIG. 45, opposite to the blade-receiving end of the locking component.
Figure 48:
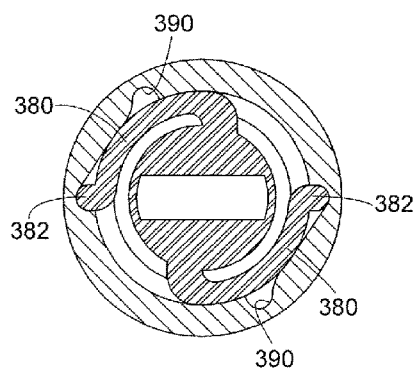
FIG. 48 is a cross-sectional view taken along lines 48-48 of FIG. 46, illustrating a spring arm member within the cylindrical barrel member in an unlocked condition.
Figure 49:
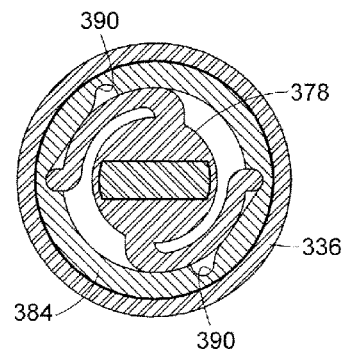
FIG. 49 is a cross-sectional view similar to FIG. 48, taken along lines 49-49 of FIG. 41, illustrating the spring arm member within the cylindrical barrel member having a blade received in a central, generally rectangular axially-extending blade-receiving slot therein, in an unlocked condition, and illustrating the cylindrical barrel member being disposed in an elongate tubular handle of the hand piece of FIG. 41.

As best illustrated in FIGS. 45, 48 and 49, the spring arm member 376 is fitted into the internal opening of notched cylindrical barrel member 384, such that the lock-stop ridges 382 of the resilient spring arms 380 are releasably seated within respective pairs of axially-extending inner notches 388 (provided along an inner wall of the cylindrical barrel member 384). In order to prevent the spring arm member 376 from falling beyond the cylindrical barrel member 384 and rattle loosely within the elongate tubular handle 336, the cylindrical barrel member 384 is provided with a radially inwardly-extending retaining lip 392 at a proximal end thereof, as best illustrated in FIG. 47, the retaining lip 392 having an inner diameter less than an outer diameter of the spring arm member 376 (even when the resilient spring arms 380 of the spring arm member 376 are compressed) such that when the resilient spring arms 380 are received in the notches 390, the spring arm member 376 is constrained from moving axially out of engagement with the cylindrical barrel member 384.

At this juncture, the tip assembly 322 is assembled to the cylindrical barrel member 384 by inserting the flat-blade extension end 328 into the keyway 346 of locking component 332, that is, by manipulating the curved end 366 of blade extension end 328 against the corresponding concave surface 340 of locking component 332, until the flat blade extension end 328 is fully seated within the blade receiving slot 355 of the spring arm member 376 within the cylindrical barrel member 384. Further, as with the first embodiment, the undercut ledges 368 on the flat blade extension end 328 can be seated against a proximal underside 333 of locking component 332 when the flat blade extension end 328 is rotated out of alignment with the keyway 346, i.e. when the tip assembly 322 is rotated from an unlocked orientation (wherein the flat blade extension end 328 is in alignment with both the blade receiving slot 355 of the spring arm member 376 and the keyway 346 of the locking component 332) to a locked orientation (wherein the lock-stop ridges 382 of the resilient spring arms 380 are rotated into seating engagement with the axially-extending notches 390 of the cylindrical barrel member 384).

When the tip assembly 322 is rotated in a first direction relative to the elongate tubular handle 386 (such as clockwise), corresponding rotation of spring arm member 376, and its resilient spring arms 380, causes each of the lock-stop ridges 382 to ride up a relatively gradual ramp upon exiting notches 388 in which the lock-stop ridges 96 are initially seated, thereby flexing the resilient spring arms 380 radially inwardly, until further rotation causes the lock-stop ridges 382 to engage a next respective pair of inner notches 390 (see FIGS. 48 and 49). As is the case with respect to the notches 290 of the cylindrical barrel members 284 of the second alternate embodiment described above, the notches 390 are provided with a relatively steep slope at the entry of the notches 390. Once the lock stop ridges 382 reach the notches 390, the resilient spring arms 380 recoil radially outwardly, thereby effectively locking the lock stop ridges 382 within the notches 390 and preventing further rotation of the spring arm member 376 relative to the elongate tubular handle 336, as well as impeding, i.e. resisting, rotation back toward an unlocked position. As in the second alternate embodiment, a tactile sensation and/or an audible clicking sound may be experienced by the dental technician upon the lock stop ridges 382 coming to rest in the notches 390, confirming the locking of the tip assembly 322 with respect to the elongate tubular handle 336. Application of a deliberate twisting force to the tip assembly 322 relative to the elongate tubular handle 336, sufficient for the resilient spring arms 380 to compress radially inwardly enough for the lock stop ridges 382 to overcome the relatively steep slope at the entry of the notches 390, is necessary to rotate the tip assembly 322 to bring the flat blade extension end 328 back into alignment with the keyway 346, permitting removal of the tip assembly 322 from the elongate tubular handle 336 by pulling the overmolded cone member 330 axially outward relative to the elongate tubular handle 386.

It will be seen, then, that with any of the embodiments of the present disclosure, the respective tip assembly 22, 122, 222, or 322 can be readily inserted, rotated, and securely affixed to the elongate tubular handle 36, 136, 236, 336. Just as readily, the tip assembly 22, 122, 222, or 322 can be disassembled from the handle 36, 136, 236, or 336 such as for re-sharpening, sterilization, storage, or replacement with a different style of instrument working tip end 26, 126, 226, 326, as desired. Further, the present system, apparatus and method allows for repeated sterilizations and re-sharpenings, as needed, for each tip assembly 22, 122, 222, 322, and then re-engagement, and proper orientation and alignment, with the elongate tubular handle 36, 136, 236, 336. Further, the advantageous use of the flat-blade extension end 28, 128, 328 with the flexible locking arms 52 or 152 and/or spring arms 276, 376, allow for relative rotational seating of the respective tip assemblies 22, 122, 222, 322 within the respective cylindrical barrel member 34, 284, 384. Further, the two-way curved end 66, 166, 366 of the blade extension in 28, 128, 328 permits self-centering of the tip assembly 22, 122, 322 within the locking component 32, 132, 332. Further, the present system allows the manufacturer to produce the least number of SKU's, i.e., of only a certain number of tip assemblies and handle portions, yet still allows the dental clinician to customize a hand piece for the respective needs and desires of their own dental practice.

The replaceable and exchangeable dental hand piece treatment tips of the present disclosure, and the elongate tubular handles therefor, can be formed so as to be compatible with a sterile disposal container, such as a sharps container.

From the foregoing, it will be observed that numerous variations of modifications may be affected without the product from the spirit and scope of the disclosure. It is to be understood that no limitation with respect to the specific apparatus or method illustrated herein is intended or should be inferred. It is, of course, intended to cover by the appended claims all such modifications as fall within the scope of the claims.

What is claimed is:

1. A dental hand piece having at least one replaceable tip, comprising:
   an elongate tubular handle;
   a locking component securely received in an end of the elongate tubular handle, the locking component including a keyway-shaped slot;
   a cylindrical barrel member securely received in the end of the elongate tubular handle and disposed axially inwardly of the locking component, an interior of the cylindrical barrel member including a plurality of axially-extending notches;
   a spring arm member comprising a body portion having at least a pair of resilient spring arms at the end of each of which is formed a lock-stop ridge, and an axially-extending blade receiving slot therethrough; and
   a replaceable tip assembly secured to the cylindrical barrel member, including
      an instrument working tip end at a distal end of a main tip body;
      a shank extending from the instrument working tip end to a proximal end of the main tip body; and
      a flat-blade extension end provided at the proximal end of the main tip body;
      wherein the flat-blade extension end extends through the keyway-shaped slot provided in the locking component and through the axially-extending blade receiving slot in the spring arm member, wherein the axially-extending notches include a first lock-stop receiving notch defined on one side thereof by a gradually-sloped ramp, and a second lock-stop receiving notch defined on a side facing the first lock-stop receiving notch by a steep ramp.

2. The dental hand piece of claim 1, wherein the cylindrical barrel member includes two pairs of the first and second lock-stop receiving notches, the first and second pairs being spaced apart from one another, and the spring arm member being actuable between a first position in which the lock-stop ridges are respectively received in the first lock-stop receiving notch of one of the pairs, and a second position, angularly offset from the first position, in which the lock-stop ridges are respectively received in the second lock-stop receiving notch of one of the pairs.

3. The dental hand piece of claim 1 wherein, when the spring arm member is in the second position, rotation of the spring arm member toward the first position is impeded by the relatively steep ramps defining the second lock-stop receiving notches.

4. The dental hand piece of claim 1, wherein the cylindrical barrel member is secured within the elongate tubular handle by at least one of an interference fit, brazing and adhesive.

5. A dental hand piece having a replaceable tip at either end thereof, comprising:
   an elongate tubular handle having a first end and a second end;
   a cylindrical barrel member securely received in each of the first and second ends of the elongate tubular handle, an interior of the cylindrical barrel member including a plurality of axially-extending notches; and
   a replaceable tip assembly including
      an instrument working tip end at a distal end of a main tip body;
      a shank extending from the instrument working tip end to a proximal end of the main tip body; and
      a spring arm member extending proximally from the shank, the spring arm member comprising a body portion having at least a pair of resilient spring arms at the end of each of which is formed a lock-stop ridge, the spring arm member received in the cylindrical barrel member, wherein the axially-extending notches include a first lock-stop receiving notch defined on one side thereof by a gradually-sloped ramp, and a second lock-stop receiving notch defined on a side facing the first lock-stop receiving notch by a steep ramp.

6. A dental hand piece having a replaceable tip at either end thereof, comprising:

an elongate tubular handle having a first end and a second end;

a cylindrical barrel member securely received in each of the first and second ends of the elongate tubular handle, an interior of the cylindrical barrel member including a plurality of axially-extending notches; and a replaceable tip assembly including an instrument working tip end at a distal end of a main tip body;

a shank extending from the instrument working tip end to a proximal end of the main tip body; and a spring arm member extending proximally from the shank, the spring arm member comprising a body portion having at least a pair of resilient spring arms at the end of each of which is formed a lock-stop ridge, the spring arm member received in the cylindrical barrel member, wherein the cylindrical barrel member includes two pairs of first and second lock-stop receiving notches, the first and second pairs being spaced apart from one another, and the spring arm member being actuable between a first position in which the lock-stop ridges are respectively received in the first lock-stop receiving notch of one of the pairs, and a second position, angularly offset from the first position, in which the lock-stop ridges are respectively received in the second lock-stop receiving notch of one of the pairs.

7. The dental hand piece of claim 6 wherein, when the spring arm member is in the second position, rotation of the spring arm member toward the first position is impeded by steep ramps defining entries to the second lock-stop receiving notches.

8. A dental hand piece having a replaceable tip at either end thereof, comprising:

an elongate tubular handle having a first end and a second end;

a cylindrical barrel member securely received in each of the first and second ends of the elongate tubular handle, an interior of the cylindrical barrel member including a plurality of axially-extending notches; and a replaceable tip assembly including an instrument working tip end at a distal end of a main tip body;

a shank extending from the instrument working tip end to a proximal end of the main tip body; and a spring arm member extending proximally from the shank, the spring arm member comprising a body portion having at least a pair of resilient spring arms at the end of each of which is formed a lock-stop ridge, the spring arm member received in the cylindrical barrel member, wherein the replaceable tip assembly includes an overmolded cone member thereon, and wherein the cylindrical barrel member includes at least one radially inwardly directed locking lip at a distal end thereof, and wherein the resilient spring arms of the spring arm member are spaced proximally from a proximal end surface of the overmolded cone member a sufficient distance to accommodate the radially inwardly directed locking lip between the resilient locking arms and the proximal end surface of the overmolded cone member as the spring arm member rotates from an unlocked position, wherein axial movement of the spring arm member relative to the cylindrical barrel member is unconstrained by any of the at least one radially inwardly directed locking lips, toward a locked position, and wherein axial movement of the spring arm member relative to the cylindrical barrel member is prevented by the at least one radially inwardly directed locking lips.

* * * * *